United States Patent [19]
Lacombat et al.

[11] 4,221,487
[45] Sep. 9, 1980

[54] SYSTEM FOR TESTING A PATTERN RECORDED ON A PLATE

[75] Inventors: Michel Lacombat; Serge Volmier-Desperques, both of Paris, France

[73] Assignee: Thomson-CSF, Paris, France

[21] Appl. No.: 22,328

[22] Filed: Mar. 20, 1979

[30] Foreign Application Priority Data

Mar. 24, 1978 [FR] France ............................ 78 08672

[51] Int. Cl.³ .................... G01B 11/00; G06K 7/10
[52] U.S. Cl. .............................................. 356/394
[58] Field of Search ................ 356/394, 398, 71; 250/559, 562

[56] References Cited
U.S. PATENT DOCUMENTS

| | | | |
|---|---|---|---|
| 3,753,617 | 8/1973 | Ehrat | 356/394 |
| 3,944,369 | 3/1976 | Cuthbert et al. | 356/394 |
| 4,139,779 | 2/1979 | Ehrat | 356/71 |
| 4,166,541 | 9/1979 | Smith | 356/398 |

*Primary Examiner*—John K. Corbin
*Assistant Examiner*—R. A. Rosenberger
*Attorney, Agent, or Firm*—Cushman, Darby & Cushman

[57] ABSTRACT

A system for testing a pattern recorded on a plate with a high density in relation to a reference pattern, comprising means for analyzing the pattern with a line detector and a logic circuit for processing the data supplied by the detector and data relating to the reference pattern, the two patterns being described line-by-line. The logic circuit is intended to detect the errors while admitting for each line a shift between the two patterns of one unit in a direction X or in a direction Y perpendicular to X, the maximum shift allowed for the entire pattern amounting, for example, to three units in each direction.

10 Claims, 16 Drawing Figures

SYSTEM FOR TESTING A PATTERN RECORDED ON A PLATE

BACKGROUND OF THE INVENTION

1. Field of the Invention

This invention relates to the testing in microlithography for the production of circuits having a very high integration density.

2. Description of the Prior Art

The production of circuits such as these involves several stages which differ according to the methods used. In photolithography, optical or electronic drawing machines produce plates carrying a single pattern, generally on a scale of 10, which will be referred to hereinafter as the reticle. A photorepeater then produces a mask carrying a regular matrix of identical patterns reproducing the pattern of the reticle on a scale of 1 in the form of opaque zones and transparent zones. This mask enables certain parts of a semiconductor substrate coated with a photosensitive resin to be selectively exposed. In a variant of this method which is known as direct photorepetition, the pattern may be directly transferred from the reticle to the substrate coated with photoresist without using an intermediate mask. The present invention is particularly intended for detecting bugs in the reticle and in the mask. It enables a rapid analysis to be made with a resolution of less than 1 $\mu$m. The position of the bug does not have to be perfectly defined. Accordingly, it is sufficient for an operator to be able to locate the bug in the field of a microscope in view of repairing it.

Reticles may have the following bugs:
errors in the positioning of the pattern elements relative to the alignment reference marks;
too few or too many pattern elements;
distorsion of the form of the pattern or incorrect dimensions;
errors in design and handling;
treatment faults (holes, excessive or inadequate etching irregularity).

Masks on a scale of 1 obtained from a theorically faultless reticle may in turn present bugs of the same kind. Additional bugs may arise, particularly in the positioning of the image, rotation of the image, enlargement, distorsion, etc.

Tests have shown that the error level and lack of rapidity of testing by visual observation, for example using microscopes, become prohibitive for circuits having a high integration density. There are techniques for scanning masks by a quasi-spot beam of electrons or photons, but unfortunately they lead to great number of data which are difficult to process.

SUMMARY OF THE INVENTION

In accordance with the present invention, the plate (mask or reticle) is divided up into bands which are successively analysed by a scan of the type used in television with a light beam of rectangular cross-section. Analysis is effected by an optical transmission measuring head using a line photodetector which enables the entire width of the band forming N individual measuring points to be simultaneously analyzed. Two identical measuring heads are used for testing pattern-repeat masks, respectively analyzing two supposedly identical patterns of the same mask. All the patterns of a mask are thus compared in twos. It would also be possible to analyse two masks carrying the same patterns. The signals delivered by the respective detectors are compared with one another and treated by a logic device enabling the differences to be determined while allowing shifts from one pattern to the other. For the testing of the reticles, the signals delivered by the detectors are compared with the information given by a magnetic recording tape convertible into imaginary images expressed in the same units as the analyzed image. The comparisons between the signals relating to the pattern to be tested and the signals relating to the reference pattern are made by a logic circuit which supplies bug indications relating to possible shifts and to the location of possible errors.

For a better understanding of the present invention, and to show how the same may be carried into effect, reference will be made to the following description in conjunction with the appended drawings.

BRIEF DESCRIPTION OF THE DRAWINGS

FIGS. 7 and 8 specify FIG. 6;

DESCRIPTION OF A PREFERRED EMBODIMENT

Figure 1:
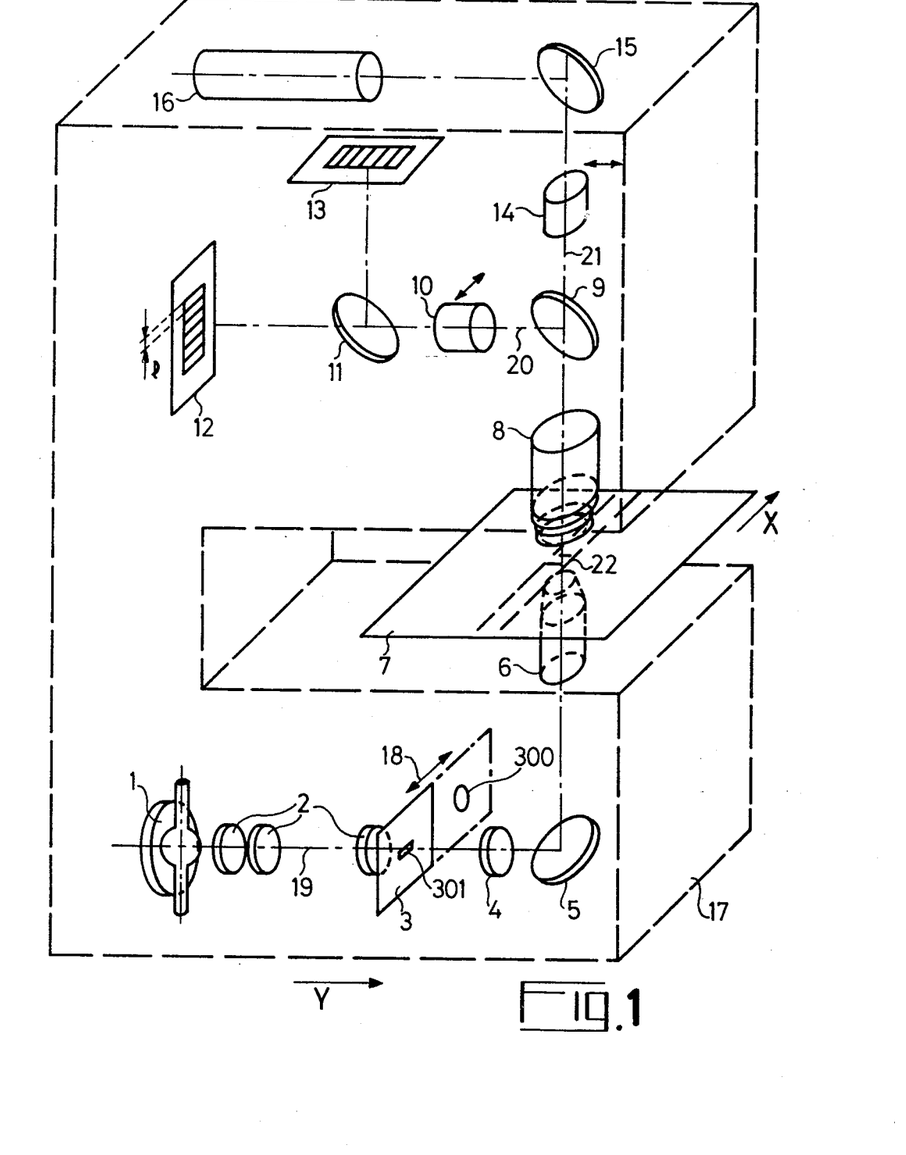
FIG. 1 is a view of an optical system for testing a plate.

FIG. 1 is a schematic view of an optical system for analyzing a plate 7 comprising opaque zones and transparent zones, which form either a single pattern, or a large number of patterns uniformly arranged in lines and columns. The plate 7 is placed on an interferometric table of the type used in a photo-repeater (not shown in the drawing). It is illuminated by a light beam of which only the axis 19 is visible in the Figure. All the elements of the optical system are integral and arranged in a mechanical support 17. The system comprises a light source 1, for example a mercury lamp. The beam emitted by the source 1 passes through a group of lenses 2 and is shaped by one of the two apertures 300 and 301 formed in a shutter 3. The aperture 300 is a circular orifice and is used for visual observation. The aperture 301 is a slot of which the dimensions enable the portion of the plate which it is desired to illuminate to be covered in view of detection. The shutter is displaceable perpendicularly of the axis 19 in the direction of the arrow 18 to enable the required aperture to be selected. The shutter 3 is followed in the direction of the light beam by a lens 4 and a mirror 5 which reflects the light towards the plate 7 through a condenser 6, enabling a rectangular zone 22 of the plate 7 to be illuminated. Depending on the transparency of the zone 22, the light is either absorbed or transmitted by the plate 7 towards a lens 8 of manification $G_8$ with a good numerical aperture so that the profile of the images is as sharp as possible which improves resolution. The focus of the lens 8 is adjusted by a method well known in the field of photo-repetition using a pneumatic sensor (not shown). The light beam is then divided by a semireflecting plate 9 into two beams. The reflected beam, of axis 20, passes through a lens 10 of variable magnification $G_{10}$ which forms the image of the zone 22 on a line detector 12 comprising N detecting cells each having an elementary width 1. The detector 12 is preferably of the CCD type, i.e. a charge-coupled device in the form of a shift register. It has to enable the detection of the entire zone 22 at one and the same time and the outlet in series of the individual data by virtue of the step-by-step shift effect. The beam transmitted by the plate 9 (axis 21) passes through a lens 14 of variable magnification $G_{14}$ and is reflected by a mirror 15 to a visual observation device 16, for example in the form of a vidicon tube which enables that zone of the specimen illuminated through the aperture 300 to be examined on a screen. Where the optical system is used for analyzing a mask or reticle, the following requirements have been decided: resolution must amount to 0.6 μm for masks and to 1.25 μm for reticles and the zone 22 must have a length D at least equal to 1000 times the resolution (D=0.6 mm or D=1.25 mm). Accordingly, the detector 12 consists of an array of 1000 detecting cells, each cell being associated with an elementary point of the zone 22. Since the CCD sensors have a minimum width of approximately 13 μm, gain values $G_8=20$ and $G_{10}=1$ are selected for the analysis of a reticle, $G_{10}=0.5$ for the analysis of a mask and $G_{14}$ is around 20 for visual observation. The lens 8 has a numerical aperture of 0.6 and the condenser 6 an aperture of 0.9. It may be of advantage to illuminate a zone 22 having a length L slightly greater than the useful length D and to use an array of more than 1000 sensors, for example 1024. By virtue of the additional width, it is possible to superpose the successively analyzed zones and to allow shifts of several units of resolution. In order to improve resolution, it is possible to use another detector 13 similar to the detector 12 illuminated by part of the beam separated by a semireflecting plate 11. The positioning of the detector 13 corresponds to a shift in space equal to half the spacing 1 between the detecting cells. Each photodetector supplies N analog signals corresponding to the transmission factor of the N elementary points of the zone 22 of the plate 7. The way in which these signals are utilised for testing purposes is described hereinafter.

Figures 2A, 2B:
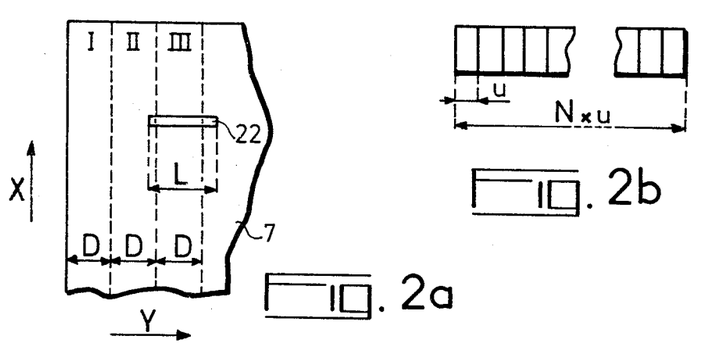
FIGS. 2a, 2b and 3 illustrate the analysis technique.

FIGS. 2a and 2b show details of the analyzed plate 7. FIG. 2a shows part of the plate 7 divided up into parallel bands I, II, III . . . of width D. It also shows the zone 22 whose length L is slightly greater than the width D and of which the image is formed on the photodetector 12. The zone 22 is shown in FIG. 2b. It is formed by N elementary "points" of which the width u is equal to 1 unit of resolution. A scan is effected as follows: the interferometric table, on which the plate 7 is placed, is displaceable in the direction X, i.e. in the direction of the bands I, II, III. The mechanical support 17 is displaceable in steps in a direction Y perpendicular to X. The successive bands are thus successively analyzed: when the band I has been completely analyzed by the relative displacement of the plate 7 and the optical system in the direction X, the support 17 is displaced in the direction Y, the table supporting the plate 7 returns to its starting position and the band II may be analyzed in the same way as in the band I, etc. The speed of the table is selected in dependence upon the desired working time per point, for example 50 ns. A counter associated with the interferometer in position X delivers a train of synchronizing pulses which define lines following one another along a band in the direction X. By virtue of the integration effect of the photodetector, the signals may be considered to remain constant over the width of a line which is equal for example to 1 resolution unit. The movement in the direction X is produced by a motor controlled by the pulses delivered by the counter. The mechanical support 17 may be moved by a step-by-step motor, whilst fine positioning may be obtained by piezoelectric ceramics.

Figure 3:
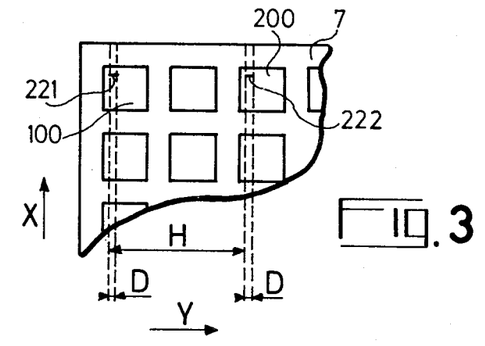

For testing a reticle, the analyzed plate 7 is the reticle itself carrying a single pattern. The signals coming from the photodetector, which are converted into logic signals, are compared with the signals issuing from a description system comprising a magnetic tape containing the data relative to the reference pattern, as will be seen hereinafter. For testing a mask carrying a large number of supposedly similar patterns, the patterns are compared in twos. In this case, a second analysis system like that shown in FIG. 1 is used, being arranged in the same support. FIG. 3 shows the traces of the two illuminating beams on the analyzed plate 7. The zones in question are the zone 221 on a pattern 100 considered as the pattern to be tested and the zone 222 on another pattern 200 considered as the reference pattern. The distance H between these two zones is equal to one or more times the spacing of the matrix of patterns. The two patterns are analyzed simultaneously because they belong to one and the same sample displaceable in the direction X and because the two optical systems are mechanically integral with one and the same support displaceable in the direction Y. It would also be possible to compare two masks providing they are supported by a common table.

Figure 4:
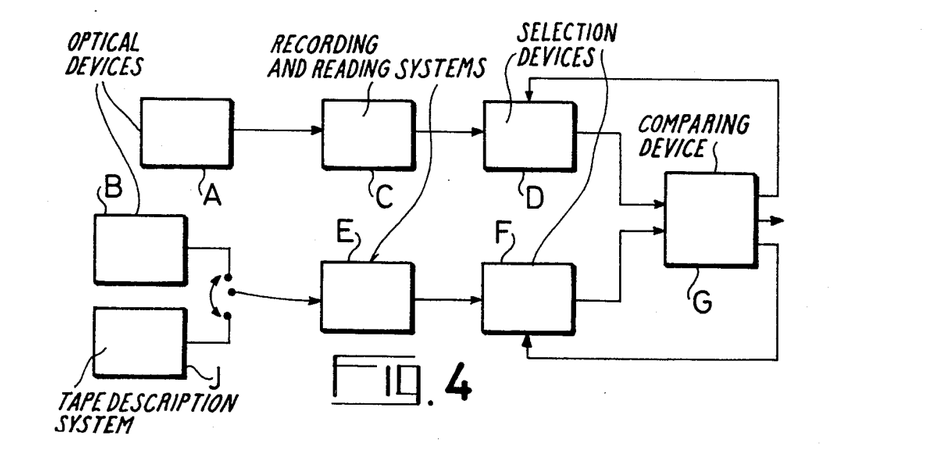
FIG. 4 is a block diagram of the complete testing system.

FIG. 4 is a block diagram of the complete testing system. An optical system A, such as that shown in FIG. 1, analyses the pattern to be tested. It supplies data to a recording and reading system C essentially consisting of shift registers which enables data relating to several successive lines to be simultaneously obtained. The system C is followed by a data selection device D which has to select the data to be used from all the data delivered by the system C. Another recording and reading system E is supplied with the signals relative to the reference pattern which come either from an optical system B similar to the system A for the testing of masks or from a magnetic tape description system J for the testing of reticles. The system E is followed by a data selection device F. The data supplied by the selectors D and F are processed in a comparing device G which delivers on the one hand information relating to the comparison of the two patterns and on the other hand selection instructions to the selectors D and F in dependence upon the results of the comparisons. The systems A and B having already been described, the following description is confined to the systems C, D, E, F, G and J.

Figure 5:
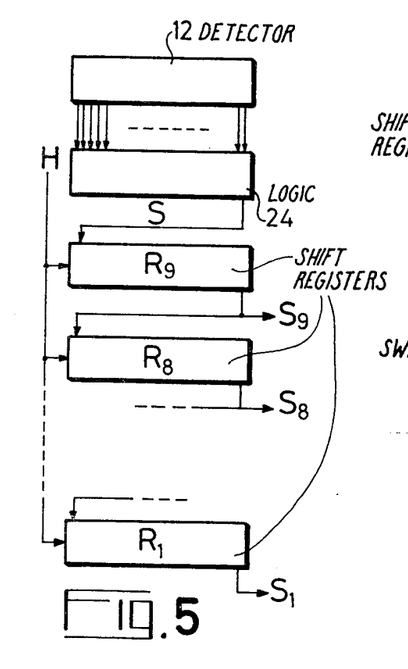
FIG. 5 shows a recording and reading system for the data relative to the pattern to be tested.

FIG. 5 shows a system for recording and reading the information relative to the pattern to be tested.

The signals coming from the detector 12 are supplied to a logic circuit 24 which, in dependence upon a predetermined decision threshold, respectively converts them into bits indicating the opacity or transparency of the corresponding analyzed points. All the bits associated with one and the same line which arrive simultaneously in the circuit 24 are stored there for sequential delivery to a first shift register $R_9$. This register is followed by another 8 shift registers $R_8$ to $R_1$, the output of one register $R_i$ being connected to the input of the register $R_{i-1}$. The capacity of each register is equal to the number of bits corresponding to one line of a band. Thus, when the register $R_9$ contains a whole line and when the first bit of the following line arrives at the input S of this register, the registers $R_8$ to $R_2$ respectively contain the 8 preceding lines. Bits associated with the points tested on one and the same column in 9 successive lines are available at the respective outputs $S_1$ to $S_9$ of the registers $R_1$ to $R_9$. All the registers are controlled by one and the same clock signal H. They are recorded and read simultaneously. At the beginning of testing, the tested line is that contained in the register $R_5$ which is the central register. As will be seen hereinafter, the tested line may emanate from another register ($R_2$ to $R_8$), depending on possible shifts detected in the direction Y, which enables a maximum shift in the direction Y of three units frontwards or backwards to be admitted at the end of testing. Accordingly, increasing numbers will be allotted to the successive lines which will thus be called $L_1, L_2 \ldots$. During the analysis of $L_1$ emanating from the register $R_5$, the line $L_6$ enters the register $R_9$. Since the time taken to record and read a line is equal to T, the beginning of testing of the line $L_1$ is staggered by 6XT in relation to its recording in the memory 24.

Figure 6:
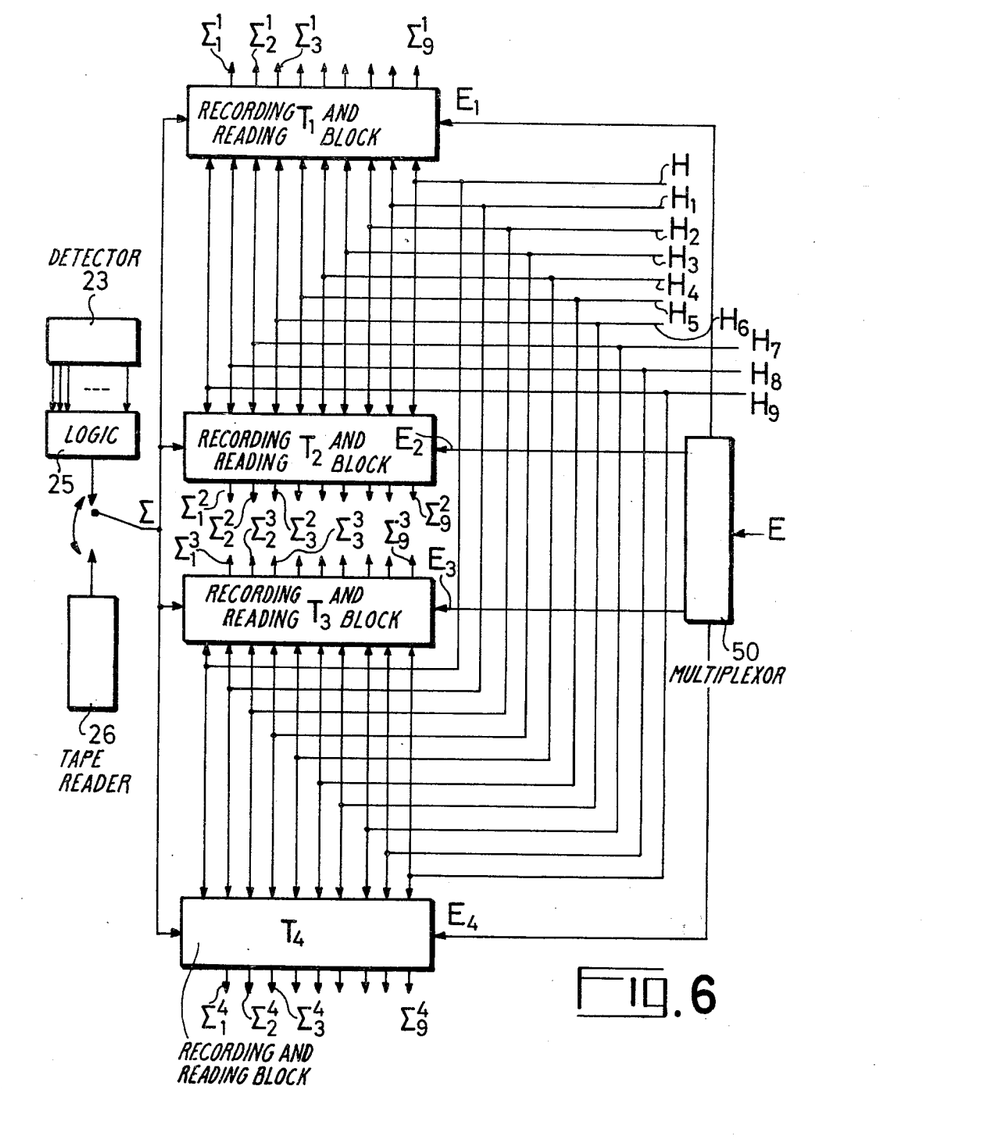
FIG. 6 shows a recording and reading system for the data relative to the reference pattern.
Figure 7:
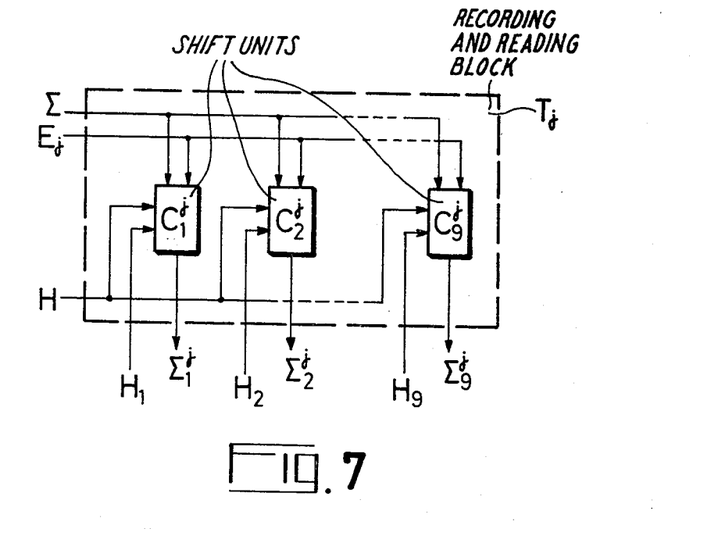
Figure 8:
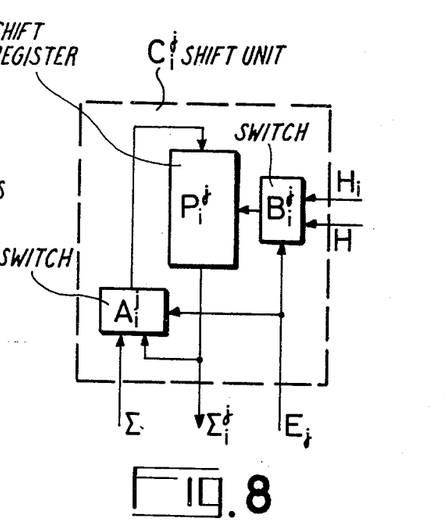

The system for recording and reading the data $\Sigma$ relative to the reference pattern is different. It is illustrated in FIG. 6. These data $\Sigma$ may emanate from two sources. In the relative testing of 2 patterns of one and the same mask, the analog signals are coming from a detector 23 and are compared with the same reference threshold as those coming from the detector 12. The bits obtained are stored in a logic circuit 25 which supplies in series the bits $\Sigma$ relating to the successive lines. In the absolute monitoring of a reticle, the series of bits $\Sigma$ is obtained from a magnetic tape reader 26. The data recorded in coded form on the tape are logically processed in this reader and are thus converted into data identical with those which would be obtained by direct analysis of the pattern, i.e. line by line and then band by band. The bits $\Sigma$ are supplied to four recording and reading blocks $T_1, T_2, T_3$ and $T_4$ essentially comprising shift registers. A multiplexor 50 synchronised by a clock signal E of period T, which is the time taken to record and read one line common to the systems shown in FIGS. 4 and 6, supplies four pulse-type selection signals $E_1, E_2, E_3$ and $E_4$ enabling the four blocks $T_1$ to $T_4$ to perform their recording and reading functions in cycles. Recording is synchronised by a clock H common with the system for analyzing the pattern to be monitored. Reading is synchronised by pulse trains $H_1, H_2 \ldots H_9$ of the same frequency as H, but staggered from one another by one period. $H_5$ is in phase with H; $H_4, H_3, H_2, H_1$ respectively show a phase lead over H of 1, 2, 3, 4 periods: $H_6, H_7, H_8, H_9$ respectively show a phase lag behind H of 1, 2, 3, 4 periods. During the analysis of a group $T_j$, the signals present at the outputs $\Sigma_1^j, \Sigma_2^j, \ldots, \Sigma_9^j$ correspond to the same line, but with respective shifts in the direction X of $-4, -3, -2, -1, 0, 1, 2, 3, 4$ units relative to the corresponding line of the pattern to be tested. FIGS. 7 and 8 show details of the general arrangement illustrated in FIG. 6. FIG. 7 shows the structure of a block $T_j$. It comprises 9 shift units $C_1^j$ to $C_9^j$ synchronised either by the clock H for recording or respectively by the clock $H_1$ to $H_9$ during the recording of the other groups. The selection between H and $H_i$ is made in the unit $C_i^j$ by the selection signal $E_j$ through a switch $B_i^j$ shown in FIG. 8 This Figure shows the structure of a unit $C_i^j$. It comprises a shift register $P_i^j$ capable of containing all the bits of one line of the reference pattern like the registers $T_i$ for the pattern to be tested. A switch $A_i^j$ enables the bits $\Sigma$ to be supplied to the register $P_i^j$ for recording every four line. During the recording of the following three lines in the three other groups, the switch $A_i^j$ enables the output of the register $P_i^j$ to be connected to its input so as not to lose the information contained therein. The switch $B_i^j$, which switches at the same time as $A_i^j$, selects either the clock H during recording or the clock $H_i$. The switches $A_i^j$ and $B_i^j$ are controlled by the binary signal $E_j$ coming from the multiplexor 50 which has, for example, the following form: $E_j=1$ for the duration of a line, every four line, which corresponds to the recording phase of the register $P_i^j$: $A_i^j$ selects $\Sigma$ and $B_i^j$ selects H; $E_j=0$ during the recording of the following three lines in the other three groups: $A_i^j$ selects $\Sigma_i^j$ and $B_i^j$ selects $H_i$. All the switches may be formed in the same way, for example with two "AND" gates followed by one "OR" gate.

Figure 9:
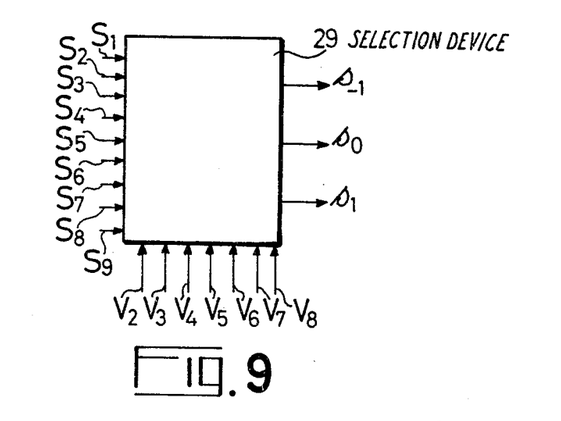
FIG. 9 shows an arrangement for selecting the signals to be examined for the pattern to be tested.

As mentioned above, not all the registers are used for verifying one line. FIG. 9 shows a selection device 29 for the registers to be examined relating to the pattern to be tested. From the outputs $S_1$ to $S_9$ of the registers $R_1$ to $R_9$ shown in FIG. 4, this device selects three, marked $s_1, s_0$ and $s_1$ in the Figure. At the beginning of analysis, the three central registers are examined, i.e. $s_{-1}=S_4$ $s_0=S_5, s_1=S_6$. Then, depending on the results of the analysis of a line, it is possible either to retain the same registers or to effect a shift by one register frontwards or backwards. The selection of the three registers is controlled by seven binary signals $V_2, V_3, V_4, V_5, V_6, V_7, V_8$ of which one is in the "1" state whilst the others are in the "0" state (or vice versa). The index k of the signal $V_k$ which is in the "1" state corresponds to the index of the signal $S_k$ which will be selected for $s_0$, so that $s_{-1}=S_{k-1}$ ans $s_1=S_{k+1}$. The signals $V_2$ to $V_8$ come from the comparing device G, as will be seen hereinafter. This selection device 29 may be made up of logic gates.

Figure 10:
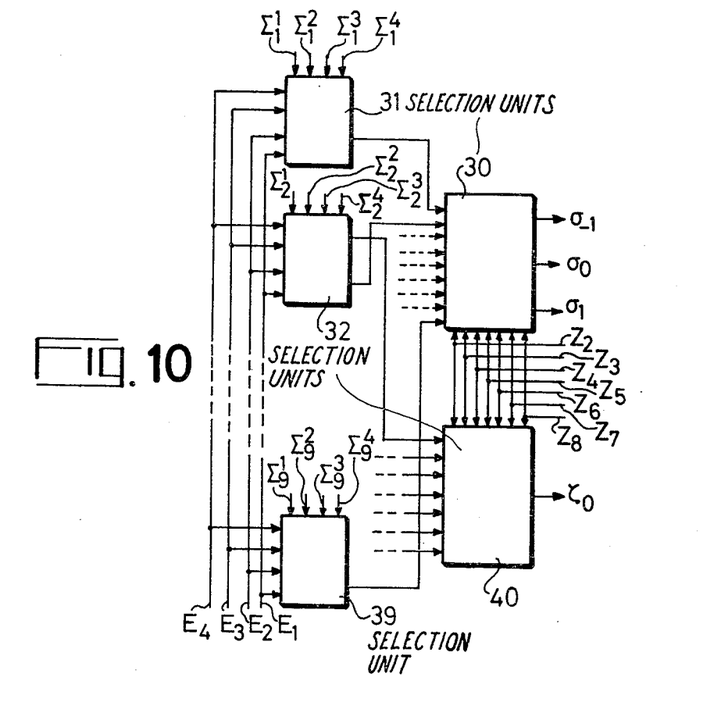
FIG. 10 shows an arrangement for selecting the signals to be examined for the reference pattern.

So far as the reference pattern is concerned, it is necessary initially to select, from the recording and reading blocks $T_1, T_2, T_3, T_4$, that which contains the line to be analysed and that which contains the following line and then, from the nine registers of the first group, the three registers to be examined and, from the nine registers of the other group, one register to be examined. The selection device is shown in FIG. 10. It comprises nine selection units 31 to 39 controlled by the binary signals $E_1, E_2, E_3, E_4$, and having an output respectively supplying the signals $\Sigma_1^j$ to $\Sigma_9^j$ where j is such that $E_{j-1}=1$. The units 32 to 38 have a further output respectively supplying the signals $\Sigma_2^{j+1}$ to $\Sigma_8^{j+1}$. During the recording of one group $T_{j-1(mod\,4)}$ (in which case $E_{j-1}=1$ and the other three signals are in the "0" state), the line contained in the group $T_j$ is analysed and the following line contained in the group $T_{j+1(mod.\,4)}$ is also read. The signals $\Sigma_1^j$ to $\Sigma_9^j$ are supplied to a selection unit 30 with three outputs $\sigma_{-1}, \sigma_0, \sigma_1$ and the signals $\Sigma_2^{j+1}$ to $\Sigma_8^{j+1}$ are supplied to a selection unit 40 with one output $\tau_0$. The units 30 and 40 are both controlled by seven binary signals $Z_2$ to $Z_8$ of which one is in the "1" state whilst the others are in the "0" state. The index k of the signal $Z_k$ which is in the "1" state corresponds to that of the signals $\Sigma_k^j$ which will be selected for $\sigma_0$ and to that of the signals $\Sigma_k j+1$ which will be selected for $\tau_0$. Accordingly, $\sigma_{-1}=\Sigma_{k-}j$ and $\sigma_1=\Sigma_{k+}j$. At the beginning of analysis, k=5. From the analysis of the second line, the signals $Z_2$ to $Z_8$ emanate from the comparing device. The selection units 31 to 39, 30 and 40 may be made up of logic gates.

Figure 11:
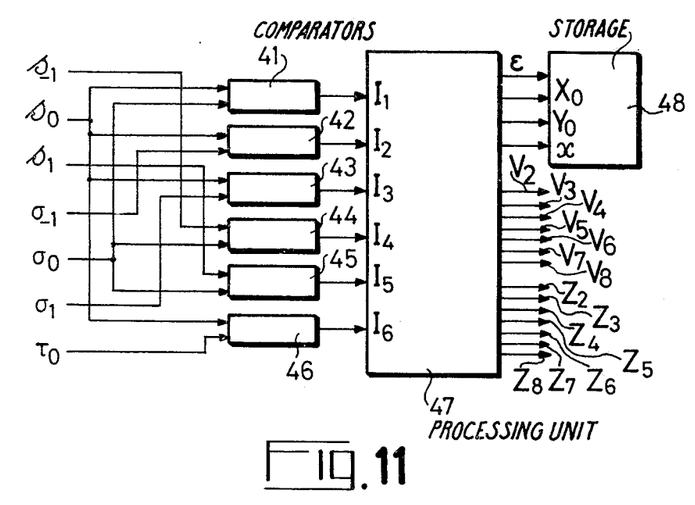
FIG. 11 shows an arrangement for comparing the signals selected for the two patterns.

The comparing device is shown in FIG. 11. It comprises six comparators 41 to 46, for example "exclusive OR" gates. Three of these comparators compare the signal $s_0$ corresponding to the line to be analysed of the pattern to be tested with the signals $\sigma_0$, $\sigma_{-1}$, $\sigma_1$ corresponding to the line to be analysed of the reference pattern which is read with different clocks. Two other comparators compare the signal $\sigma_0$ with the signals $s_{-1}$ and $s_1$ corresponding respectively to the preceding line and to the following line of the line to be analysed of the reference pattern. The sixth comparator compares the signal $s_0$ with the signal $\tau_0$ corresponding to the following line of the line to be analysed of the reference pattern which is read with the same clock as $\sigma_0$. The signals $I_1$ to $I_6$ resulting from the comparisions supply information on the pattern to be tested. In addition, they are supplied to a processing unit 47 which supplies the selection signals $V_2$ to $V_8$ and $Z_2$ to $Z_8$ controlling the selection devices shown in FIGS. 9 and 10. The mode of operation of the comparing device will be described with reference to examples. The similarity between the analysed line of the pattern to be tested and the analysed line of the reference pattern is verified when the signal $I_1$ is in the "0" state throughout the reading of these two lines. In this case, the processing unit 47 keeps the outputs $V_2$ to $V_8$ and $Z_2$ to $Z_8$ in the same state for the analysis of the following line of two patterns. When the chronogram of the signal $I_1$ contains some "1", it is possible by studying the other signals to determine whether there is a shift of one unit in the direction X or in the direction Y between the two patterns. In this case, the processing unit 47 modifies the state of the outputs $V_2$ to $V_8$ or $Z_2$ to $Z_8$ in order to take this shift into account for the following line. The absence of a shift is indicative of an error and the following line is analysed without any change in the state of the signals $V_2$ to $V_8$ and $Z_2$ to $Z_8$. The processing unit 47 may be made up of logic elements, particularly bistable circuits and storages. When a shift or an error has been detected, the processing unit supplies signals characterising this shift or error, for example a signal $\epsilon$ characterising the type of shift (frontwards, backwards, direction X, direction Y) or the error and signals $X_0$, $Y_0$, x respectively characterizing the abscissa of the band, the ordinate of the line and the abscissa in the line where the shift or error is situated. The signals $\epsilon$, $X_0$, $Y_0$, x may be stored in a memory 48 for subsequent use.

FIGS. 12 to 15 illustrate examples of the configuration of patterns and differences which may exist between the pattern to be tested 100, shown at (a), in the FIGS., and the reference pattern 200 shown at (b) in the FIGS. For all these examples, the situation is as follows:
analysis of the lines $L_1$ to $L_3$ has not revealed any bug, so that $V_5=1$ and $Z_5=1$;
the logic signals of which the chronograms are shown below the two patterns relate to the lines $L_4$ of the two patterns ($E_4=1$);

At the beginning of analysis of the line $L_4$, the registers $R_2$ to $R_9$ respectively contain the lines $L_1$ to $L_8$, $R_1$ being empty and the line $L_9$ enters the register $R_9$; the groups $T_3$, $T_4$, $T_1$, $T_2$ respectively contain the lines $L_3$, $L_4$, $L_5$, $L_6$ and the line $L_7$ enters $T_3$.

Since no shift has as yet been detected, the selected registers are $R_4$, $R_5$, $R_6$ respectively containing the lines $L_3$, $L_4$, $L_5$ of the pattern 100 and respectively supplying the signals $s_{-1}$, $s_0$, $s_1$, $C_4^4$, $C_5^4$, $C_6^4$ containing the line $L_4$ of the pattern 200 and respectively supplying the signals $\sigma_{-1}$, $\sigma_0$, $\sigma_1$ and $C_5^1$ containing the line $L_5$ of the pattern 200 and supplying the signal $\tau_0$. The chronograms shown at (c), (d), ... (p) are respectively those of the signals $s_{-1}$, $s_0$, $s_1$, $\sigma_{-1}$, $\sigma_0$, $\sigma_1$, $\tau_0$, $I_1=s_0\oplus\sigma_0$, $I_2=s_0\oplus\sigma_1$, $I_3=s_0\oplus\sigma_1$, $I_4=s_1\oplus\sigma_0$, $I_5=s_{-1}\oplus\sigma_0$, $I_6=s_0\oplus\tau_0$.

Figure 12:
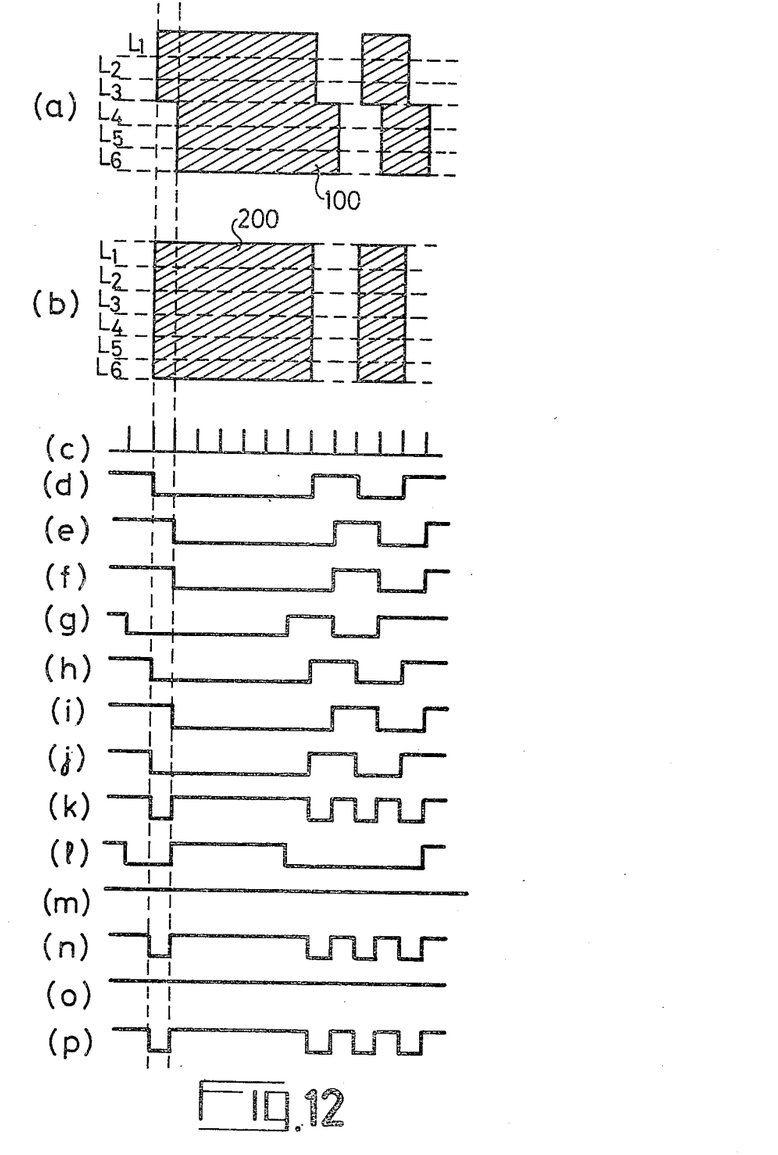
FIGS. 12 to 15 illustrate the operation of the comparing device with reference to examples of bugs.

FIG. 12 illustrates a backward shift in the direction X of the pattern 100 to be tested in relation to the reference pattern 200 from the line $L_4$. The presence of "0" in the signal $I_1$ indicates that the lines $L_4$ of the two patterns are not identical. The absence of "0" in the signal $I_3$ indicates that there is a shift in the direction X between the two patterns, the pattern 100 lagging behind the pattern 200 by 1 unit. It is advisable to take this shift into account during the analysis of the following line. The processing unit 47 keeps the input $V_5$ of the selector 29 in the "1" state so as to re-select the registers $R_4$, $R_5$ $R_6$, the line subsequently analysed being $L_5$ emanating from $R_5$. At the contrary, the signal $Z_5$ passes into the state "0", whilst the signal $Z_6$ passes into the "1" state. On the other hand, the multiplexor supplies $E_1=1$ and $E_2=E_3=E_4=0$, so that the selected registers are $C_5^1$, $C_6^1$, $C_7^1$ containing the line $L_5$ and $C_6^2$ containing the line $L_6$, the output $\sigma_0$ of the register $C_6^1$ and the output $\tau_0$ of the register $C_6^2$ lagging behing the output $s_0$ of the register $R_5$ by one period. It can be seen from the Figure that the identity of the lines $L_5$ of the two patterns will be verified.

Figure 13:
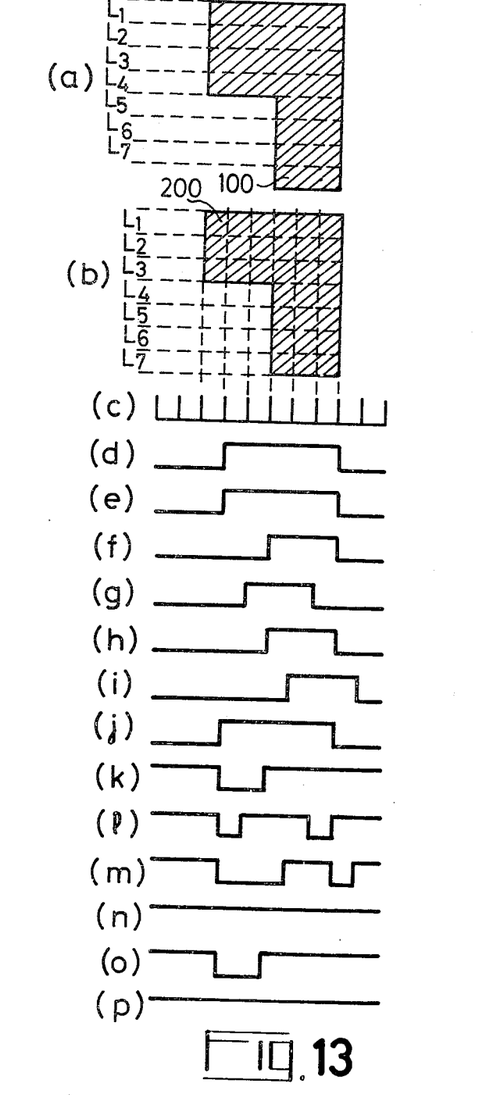

FIG. 13 illustrates a forward shift by one unit in the direction Y of the pattern 100 in relation to the pattern 200. The presence of "0" in the chronograms of the signals $I_1$, $I_2$, $I_3$ indicates a difference between the two patterns which is not a shift in the direction X. The combination of an absence of "0" in $I_4$ and a presence of "0" in $I_5$ indicates a shift in the direction Y between the two patterns, the pattern 100 lagging behind the pattern 200 by one line. For the analysis of the following line, the processing unit 47 supplies a signal $V_6$ in the "1" state so as to select the registers $R_5$, $R_6$, $R_7$ and keeps $Z_5$ in the "1" state so as to select $C_4^1$, $C_5^1$, $C_6^1$, $C_5^2$. The line $L_6$ of the pattern 100 and $L_5$ of the pattern 200 are analysed, which enables the detected lag to be compensated. These two lines are read in phase.

Figure 14:
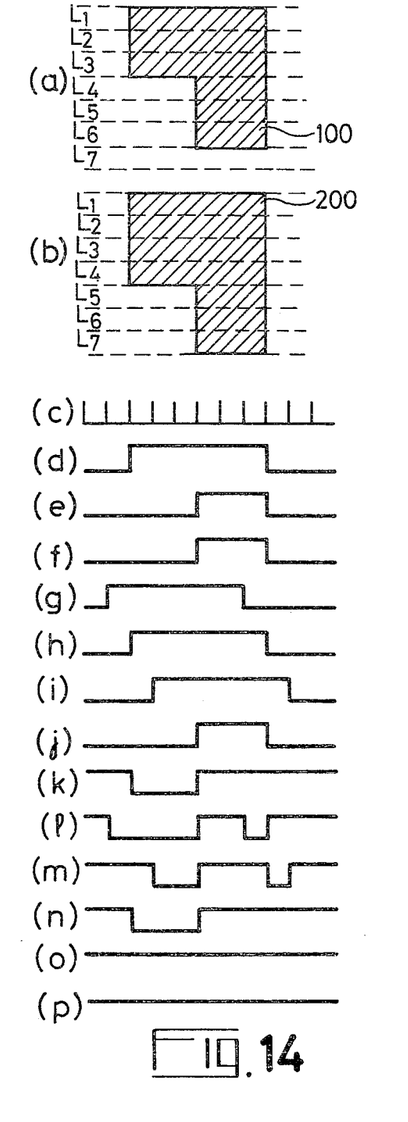
Figure 15:
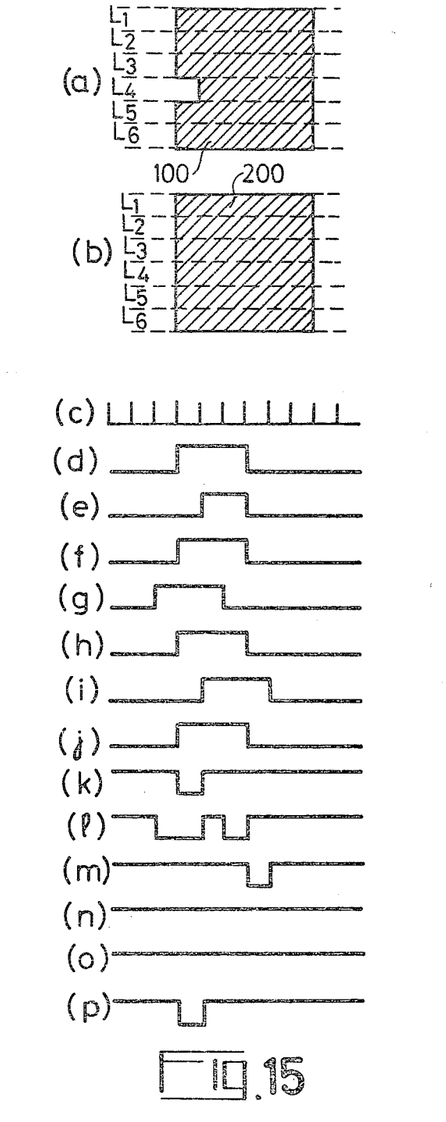

FIG. 14 illustrates a backward shift by one unit in the direction Y of the pattern 100 in relation to the pattern 200. The presence of "0" in the signals $I_1$, $I_2$, $I_3$ indicates that there is neither identity nor a shift in the direction X between the two patterns. The presence of "0" in the signal $I_4$ precludes a forward shift in the direction Y. The absence of "0" in the signal $I_6$ is indicative of a backward shift in the direction Y. For the analysis of the following line, the processing unit 47 supplies the outputs $V_4$ and $Z_5$ in the "1" state thus selecting the registers $R_3$, $R_4$, $R_5$, $C_4^1$, $C_5^1$, $C_6^1$, $C_5^2$. The system then compares the lines $L_4$ of the pattern 100 and $L_5$ of the pattern 200, these two lines being read in phase. FIG. 15 illustrates an error in the pattern 100. This example illustrates more clearly the need to make two comparisons: $s_1\oplus\sigma_0$ and $s_{-1}\oplus\sigma_0$ for determining a forward shift in the direction Y. This is because, in the example shown in FIG. 15, there is an absence of "0" in the signal $I_4 = s_1 \oplus \sigma_0$ although there is no a shift. The similar absence of "0" in the signal $I_5 = s_{-1} \oplus \sigma_0$ is indicative of an error because there cannot be two successive line modifications in the pattern and the combination $\sigma_0 = s_1 = s_{-1}$ and $\tau_0 \neq s_0$ corresponds to an error. For the analysis of the following line, there is no change in the selection signals. The lines $L_5$ of the two patterns will be compared with one another, being read in phase.

The testing system as hereinbefore described is only an embodiment of the invention. Many changes may be made in the various elements of the block-diagram of FIG. 4. In the elements, as described, the choice of the number of registers, clocks, and selection signals depends on the requirements. From a general point of view, where a shift of a single unit in a single direction is allowed per line, a maximum shift of a units frontwards or backwards in the direction X and a maximum shift of b units frontwards or backwards in the direction Y, the index i goes from 1 to $2a+3$ and the index j goes from 1 to $b+1$, so that the recording and reading system C comprises $n=2a+3$ shift registers and the recording and reading system E comprises $p=b+1$ sets of n shift registers, where n and p are integrals such that $n \geq 5$ and $p \geq 2$.

What we claim is:

1. A system for testing a pattern recorded on a plate having two levels of modulation for a luminous analysis beam in relation to a reference pattern, the two patterns being decomposible into elementary rectangles forming lines parallel to a direction Y and following one another in a direction X perpendicular to Y, said system comprising:
   a first analysis system for analyzing the pattern to be tested, comprising means for projecting said analysis beam to illuminate N successive rectangles of one and the same line on said plate, imaging means introducing a magnification G and detecting means comprising N aligned detecting cells respectively optically conjugated with said N rectangles in relation to the imaging means; said detecting means supplying a series of bits S relating to the level of modulation of the illuminated rectangles;
   displacement means for relatively displacing said plate and said analysis system in said directions X and Y so as to effect a line-by-line analysis by bands of N rectangles width;
   a second analysis system for supplying a series of bits Σ relating to the reference pattern described line-by-line by bands of N rectangles;
   a first and second processing units for processing said bits S and Σ, respectively, which simultaneously supply selected signals relating to two homologous rectangles of the pattern to be tested and of the reference pattern and signals relating to adjacent rectangles respectively having a shift of at least one rectangle in one and the same line and a shift of at least one line in the direction Y;
   comparing means for comparing said selected signals and enabling any shifts of at least one rectangle and one line respectively in said directions X and Y between said two patterns to be determined and any recording errors in the pattern which cannot be attributed to a shift to be detected.

2. A system as claimed in claim 1, wherein said displacement means comprise means for continuously displacing said plate in said direction X and means for displacing said analysis system in steps in said direction Y, said two displacements enabling said analysis beam to scan the entire surface of said plate.

3. A system as claimed in claim 2, wherein said reference pattern is recorded on the same plate as the pattern to be tested.

4. A system as claimed in claim 3, wherein said second analysis system is identical to said first analysis system, the two analysis systems being mechanically integral.

5. A system as claimed in claim 2, wherein said reference pattern is described on a magnetic tape in the form of binary signals.

6. A system as claimed in claim 5, wherein said second analysis system comprises a logic circuit for decoding said binary signals, supplying sequences of bits Σ describing the pattern line-by-line, the dimensions of the rectangles forming the lines being the same as those of the pattern to be tested.

7. A system as claimed in claims 4 or 6, wherein said first processing comprises one set of n shift registers connected in series and supplied with said bits S, n being an integer such that $n \geq 5$, the capacity of each register being equal to N, said n registers sequentially supplying, at their n respective outputs, n synchronous sequences of bits corresponding to the modulation level of the N rectangles of n successive lines; said first processing unit further comprising a first selection device selecting between n sequences, three ones: $s_{-1}$, $s_0$, $s_1$ relating to three successive lines respectively.

8. A system as claimed in claim 7, wherein said second processing unit comprises p sets of n shift registers, p being integral such that $p>2$, the capacity of each register being equal to N, each set being cyclically loaded with the bits Σ relating to one of p lines, the n registers of each set supplying, n sequences of bits resulting from a single one to which successive phase shifts have been introduced, so that, at each time, the bits supplied by said n registers of said p sets correspond to the modulation level of n successive rectangles of p successive lines, respectively; said second processing unit further comprising a second selection device selecting three sequences $\sigma_{-1}$, $\sigma_0$, $\sigma_1$ respectively provided by three successive registers of one and the same set and one sequence $\tau_0$ synchroneous with $\sigma_0$, from the following set.

9. A system as claimed in claim 8, wherein said comparing means is supplied with the sequences $s_{-1}$, $s_0$, $s_1$, $\sigma_{-1}$, $\sigma_0$, $\sigma_1$, $\tau_0$, compares $s_0$ with $\sigma_{-1}$, $\sigma_0$, $\sigma_1$, and $\tau_0$, compares $\sigma_0$ with $s_{-1}$ and $s_1$, provides signals depending upon the results of the comparisons at the end of each two lines compared from said two patterns, said signals characterizing the following results:
   identity of said two lines;
   shift by one unit in said direction X between said two patterns;
   shift by one unit in said direction Y between said two patterns; and supplies to said selection devices selection signals enabling any determined shift to be taken into account for the comparison of two following lines of said two patterns.

10. A system as claimed in claim 9, wherein $n=9$ and $p=4$.